United States Patent [19]
van Ooyen et al.

[11] Patent Number: 5,610,046
[45] Date of Patent: Mar. 11, 1997

[54] CLONING AND EXPRESSION OF XYLANASE B

[75] Inventors: Albert J. J. van Ooyen, Voorburg; Leendert H. DeGraaff, Oosterbeek; Henriette C. van den Broeck; Jacob Visser, both of Wageningen, all of Netherlands

[73] Assignee: Gist-brocades, N.V., Ma Delft, Netherlands

[21] Appl. No.: 290,979

[22] PCT Filed: Dec. 24, 1993

[86] PCT No.: PCT/EP93/03701

§ 371 Date: Oct. 28, 1994

§ 102(e) Date: Oct. 28, 1994

[87] PCT Pub. No.: WO94/14965

PCT Pub. Date: Jul. 7, 1994

[30]     Foreign Application Priority Data

Dec. 24, 1992  [EP]   European Pat. Off. ............. 92204092

[51] Int. Cl.$^6$ ............... C12N 9/24; C12N 1/19; C12N 15/63; C07H 21/04
[52] U.S. Cl. ............... 435/200; 435/254.11; 435/320.1; 435/252.3; 536/23.2
[58] Field of Search ................... 435/200, 69.1, 435/320.1, 254.11; 536/23.2, 24.1

[56]              References Cited

FOREIGN PATENT DOCUMENTS

386888A3  9/1990  European Pat. Off. ..
91201944  1/1992  European Pat. Off. ..

OTHER PUBLICATIONS

Chesson, "Supplementary Enzymes To Improve the Utilization of Pig and Poultry Diets", *Recent acvances in Animal Food Nutrition*, Haresign, W. and Cole, D. J. A., eds., Butterworth, London, 71–89 (1987).

Carre et al., "Yield and Composition of Cell Wall Residues Isolated from Various feedstuffs Used for Non–Ruminant Farm Animals", *J. Sci. Food Agric.* 37:341–351 (1986).

McCleary et al., "Enzymic Analysis of Polysaccharide Structure", *Adv. Carb. Chem. and Biochem.* 44:147–276 (1987).

Wong et al., "Multiplicity of β–1, 4–Xylanase in Microorganisms: Functions and Applications", *Microbiol. Rev.* 52:305–317 (1988).

Woodward, "Xylanases: Functions, Properties and Applications", *Topics in Enzyme Ferment. Biotechnol.* 8:9–30 (1984).

Dekker et al., "Hemicellulases: Their Occurrence, Purification, Properties, and Mode of Action", *Adv. Carb. Chem. and Biochem.* 32:278–353 (1976).

*Primary Examiner*—Charles L. Patterson, Jr.
*Assistant Examiner*—Kawai Lau
*Attorney, Agent, or Firm*—Morrison & Foerster LLP

[57]              ABSTRACT

Method and expression constructs are provided for the cloning of genes from fungal origin which encode polypeptides having the activity of the *Aspergillus tubigensis* XYL B enzyme and their overexpression in a selected microbial host cell. The present invention provides for the high level production of XYL B which may be used in a variety of industrial applications.

14 Claims, 2 Drawing Sheets

FIG. 1

(FORMULA 4)

```
TGTTTCGGAGATCAATTCGGCTTCCAAATCGCCCACGGATGCTCCACCGACTAGGCTAAAC
CCCATCACAGCGGACGTTTCAGGTACGGCAGGGTCTCACATTTAGGGCCTCGGCAGGGTC
TCGGCAGGTACCCTTCTTAATAAAGGCTAAATAGCTTCTGCAGAATCATGGGTATATCAG
GAACGTCTCCTCCGTCGCTGCAGACCTTCTCTTCTTACTCCCAGTCCCATTGAATCAACT
CCTCAAGCCAAGTCTCTTTCAACATGCTTACCAAGAACCTTCTCCTCTGCTTCGCCGCAG
                                M  L  T  K  N  L  L  L  C  F  A  A  A
CTAAGGCTGTTCTGGCCGTTCCCCACGACTCTGTCGTCGAGCGTTCCGATGCCTTGCACA
  K  A  V  L  A  V  P  H  D  S  V  V  E  R  S  D  A  L  H  K
AGCTCTCTGAGCGTTCGACCCCGAGCTCGACCGGCGAGAACAACGGCTTCTACTACTCCT
  L  S  E  R  S  T  P  S  S  T  G  E  N  N  G  F  Y  Y  S  F
TCTGGACCGACGGCGGTGGTGATGTGACCTACACCAACGGTGACGCTGGCTCGTACACCG
  W  T  D  G  G  G  D  V  T  Y  T  N  G  D  A  G  S  Y  T  V
TCGAGTGGTCCAACGTTGGCAACTTTGTTGGTGGAAAGGGCTGGAACCCTGGAAGTGCGC
  E  W  S  N  V  G  N  F  V  G  G  K  G  W  N  P  G  S  A  Q
AGTAAGTTAACCTTTCCCAAGCTGTCCCTCTAGGGTATTCAGTGAAACAAATGCTCACAT
AACTTCAGGGACATCACCTACAGCGGCACCTTCACCCCTAGCGGCAACGGCTACCTCTCC
          D  I  T  Y  S  G  T  F  T  P  S  G  N  G  Y  L  S
GTCTATGGCTGGACCACTGACCCCCTGATCGAGTACTACATCGTCGAGTCCTACGGCGAC
  V  Y  G  W  T  T  D  P  L  I  E  Y  Y  I  V  E  S  Y  G  D
TACAACCCCGGCAGTGGAGGCACCTACAAGGGCACCGTCACCTCCGATGGATCCGTCTAC
  Y  N  P  G  S  G  G  T  Y  K  G  T  V  T  S  D  G  S  V  Y
GATATCTACACGGCTACCCGCACCAACGCCGCTTCCATCCAAGGAACCGCTACCTTCACC
  D  I  Y  T  A  T  R  T  N  A  A  S  I  Q  G  T  A  T  F  T
CAGTACTGGTCCGTTCGCCAGAACAAGAGAGTCGGAGGAACTGTTACCACTTCCAACCAC
  Q  Y  W  S  V  R  Q  N  K  R  V  G  G  T  V  T  T  S  N  H
TTCAACGCTTGGGCTAAGCTGGGCATGAACCTGGGTACTCACAACTACCAGATCGTGGCT
  F  N  A  W  A  K  L  G  M  N  L  G  T  H  N  Y  Q  I  V  A
ACCGAGGGCTACCAGAGCAGCGGATCTTCCTCCATCACTGTTCAGTGAGCTTGGATGTCC
  T  E  G  Y  Q  S  S  G  S  S  S  I  T  V  Q  *
AACTGTGCTTGCAGGGATTGGGTGGATCTGGGAAATGAGTGCGATGGTCCTTGGAAATAT
TGAGCAATCATATGATGTGTGAAACAATTAGTTGCTCGCTATCAATGCACTTGTCGTTGG
AATCTATCAAGCCATCTAGTGTAGTATCCTTCATACTCCGAGAATAGTACATTACAGACT
ATCTCGGCAGATCGAGGCGCACCACTATCCGAGGGATACCTCTTTTGGTCTAGTTGTAGC
AGTCTGTGACATTAACATCAAGTATTATGCGTGCTAGCTCCCGTCATATTGTAGCAGTCA
TTCCGGAGTAGACGACACCGGTTGGTCGAGCCAAACTAAATGAGCTATAATTTCAACAGC
AGGAGTCCGGACGGCGTCTGACCTCAGTGATTCCAGTAGGCATCTTCTTTTACACGTTAG
AGAATGTCTCAATTTCAGACAACCAGCAATTATTCACATTCGGGATGTCCCACTTATCTC
TTATGATCCTTCAACACGTCTACCAATGAAAGCCACTTTTTACTATGTAAGTAAAAATCG
ACAAGCCCGTCAGCGCCATGG
```

FIG. 2

CLONING AND EXPRESSION OF XYLANASE B

The present invention relates to the field of molecular biology. In particular, the present invention relates to the cloning and overexpression of a DNA sequence encoding a protein having the activity of the *Aspergillus tubigensis* xylanase B (XYL B) protein. The present invention also provides methods for the production and use of a single xylanase which is obtainable in a form which is free of other xylanases, and indeed from other enzymes in general.

BACKGROUND OF THE INVENTION

The composition of a plant cell wall is complex and variable. Polysaccharides are mainly found in the form of long chains of cellulose (the main structural component of the plant cell wall), hemicellulose (comprising various β-xylan chains) and pectin. The occurrence, distribution and structural features of plant cell wall polysaccharides are determined by (1) plant species; (2) variety; (3) tissue type, (4) growth conditions; (5) aging and (6) processing of plant material prior to feeding.

Basic differences exist between monocotyledons (e.g. cereals and grasses) and dicotyledons (e.g. clover, rapeseed and soybean) and between the seed and vegetative parts of the plant (Chesson, 1987; Carré and Brillouet, 1986). Monocotyledons are characterized by the presence of an arabinoxylan complex as the major hemicellulose backbone. The main structure of hemicellulose in dicotyledons is a xyloglucan complex. Moreover, higher pectin concentrations are found in dicotyledons than in monocotyledons. Seeds are generally very high in pectic substances but relatively low in cellulosic material. Three more or less interacting polysaccharide structures can be distinguished in the cell wall:

(1) The middle lamella forms the exterior cell wall. It also serves as the point of attachment for the individual cells to one another within the plant tissue matrix. The middle lamella consists primarily of calcium salts of highly esterified pectins;

(2) The primary wall is situated just inside the middle lamella. It is a well-organized structure of cellulose microfibrils embedded in an amorphous matrix of pectin, hemicellulose, phenolic esters and proteins;

(3) The secondary wall is formed as the plant matures. During the plant's growth and ageing phase, cellulose microfibrils, hemicellulose and lignin are deposited.

The primary cell wall of mature, metabolically active plant cells (e.g. mesophyll and epidermis) is more susceptible to enzymatic hydrolysis than the secondary cell wall, which by this stage, has become highly lignified.

There is a high degree of interaction between cellulose, hemicellulose and pectin in the cell wall. The enzymatic degradation of these rather intensively cross-linked polysaccharide structures is not a simple process. At least five different enzymes are needed to completely break down an arabinoxylan, for example. The endo-cleavage is effected by the use of an endo-Θ(1→4)-D-xylanase. Exo-(1→4)-D-xylanase liberates xylose units at the non-reducing end of the polysaccharide. Three other enzymes (α-glucuronidase, α-L-arabinofuranosidase and acetyl esterase) are used to attack substituents on the xylan backbone. The choice of the specific enzymes is of course dependent on the specific hemicellulose to be degraded (McCleary and Matheson, 1986).

For certain applications, however, complete degradation of the entire hemicellulose into monomers is not necessary or is not desirable. In the liquefaction of arabinoxylan, for example, one needs simply to cleave the main xylan backbone into shorter units. This may be achieved by the action of an endo-xylanase, which ultimately results in a mixture of xylose monomer units and oligomers such as xylobiose and xylotriose. These shorter subunits are then sufficiently soluble for the desired use. Furthermore, it has been demonstrated that the actions of specific xylanase enzymes differ from one another, as seen by the varying patterns of xylose monomer and oligomer units resulting from the action of these specific enzymes on an arabinoxylan substrate (Kormelink, F., 1992).

Filamentous fungi are widely known for their capacity to secrete large amounts of a variety of hydrolytic enzymes such as α-amylases, proteases and amyloglucosidases and various plant cell wall degrading enzymes such as cellulases, hemicellulases, and pectinases. Among these, multiple xylan-degrading enzymes have been recognized, which have been shown to possess a variety of biochemical and physical properties. This heterogeneity in xylanase function allows for the selection of a xylanase of interest which is best suited for a desired application (see Wong et al. (1988), Woodward (1984) and Dekker and Richards (1977)).

Multiple xylanases of various molecular weights are known to be produced by micro-organisms such as *Aspergillus niger*, *Aspergillus tubigensis*, *Clostridium thermocellum*, *Trichoderma reesei*, *Penicillium janthinellum*, as well as species of Bacillus and Streptomyces. In *Aspergillus tubigensis*, for example, three distinct xylanases (XYL A, B and C) have been identified.

In nature, microbial xylanases are always produced together with other enzymes having polysaccharide-degrading activities, such as exo-arabinanase, acetyl esterase and cellulases. For some applications, such as the bleaching of lignocellulosic pulp, some of these enzyme activities are not needed or are unwanted.

It is known that fermentation conditions may be varied to favor the production of an enzyme of interest. It is also known that the cloning of the gene encoding the desired enzyme and overexpressing it in its natural host, or other compatible expression host will specifically enhance the production of the enzyme of interest. This latter method is particularly useful if the enzyme of interest is to be obtained in a form which is free of undesired enzyme activity.

The cloning of the *A. tubigensis* gene encoding the xylanase A (XYL A) enzyme has been described by Van den Broeck et al. (1992). The description is hereby incorporated by reference.

However it has been found that the *A. tubigensis* XYL B enzyme has slightly higher pH and temperature optima than does the XYL A enzyme. For certain applications such as the bleaching of lignocellulosic pulp, xylanases having higher pH and temperature optima are preferred, particularly those xylanase enzyme preparations having little or no cellulase activity.

Unfortunately, *A. tubigensis* produces the XYL B enzyme in lower quantities than either the XYL A or XYL C proteins. This coupled with the fact that the XYL B enzyme is difficult to purify from the other enzymes in the culture broth from the fermentation of *A. tubigensis* make the production of XYL B via classical fermentation and purification techniques economically unfeasible.

Efforts to clone the xlnB gene (which encodes the XYL B enzyme) from *A. tubigensis* using the protocol for hybridization to the xylA gene as described by van den Broeck et al. (1992) failed to yield a positive signal. This implies that it is not possible to isolate the xlnB gene by heterologous hybridization to the xlnA gene.

Nonetheless, it would be of great importance to obtain genes encoding an enzyme having the activity of the *A. tubigensis* XYL B enzyme which may be brought to expression in other, high-producing microbial expression hosts. In this manner, the production and use of an enzyme having the activity of the *A. tubigensis* XYL B enzyme (optionally lacking the presence of undesirable side activities may be made economically feasible for industrial applications.

SUMMARY OF THE INVENTION

The present invention provides purified and isolated DNA sequences of fungal origin, which encode proteins having the activity of the *Aspergillus tubigensis* xylanase B (XYL B) enzyme. These DNA sequences include the xylanase encoding sequence and preferably the adjacent 5' and 3' regulatory sequences as well.

It is also an object of the present invention to provide constructs for the microbial overexpression of the XYL B-encoding sequences using either their native regulatory sequences or, in an alternative embodiment, the xylanase-encoding sequence operably linked to selected regulatory regions such as promoter, secretion leader and terminator signals which are capable of directing the overexpression of the XYL B protein in a suitable expression host.

It is a further object of the present invention to provide microbial expression hosts, transformed with the expression constructs of the present invention, which are capable of the overexpression and, if desired, the secretion of the XYL B protein.

It is yet a further object of the present invention to provide methods for the production of a XYL B enzyme which may, in turn, advantageously and economically be used in an industrial process.

DETAILED DESCRIPTION OF THE INVENTION

The present invention describes a purified and isolated DNA sequence which encodes a protein having the activity of the *Aspergillus tubigensis* xylanase B (XYL B) enzyme. The DNA sequence preferably includes the XYL B-encoding sequence and adjacent 5' and 3' regulatory sequences. Genetic variants include hybrid DNA sequences containing the XYL B-encoding sequence coupled to regulatory regions, such as promoter, secretion and terminator signals, originating from homologous or heterologous organisms. Genetic variants also include DNA sequences encoding the XYL B protein where the codon selection has been chosen for optimal recognition by the selected expression host. The present invention also includes DNA sequences which are capable of hybridizing under stringent conditions to the XYL B-encoding DNA sequences and genetic variants thereof, as described above, but which may differ in codon sequence due to the degeneracy of the genetic code or inter species variation.

The present invention also provides DNA constructs for the expression of the gene encoding the XYL B protein in a desired expression host. These expression constructs include the XYL B-encoding region operably linked to regulatory regions, such as promoter, secretion and terminator signals originating from homologous or heterologous organisms, these regulatory regions being capable of directing the overexpression of the gone encoding the XYL B enzyme in an appropriate host. Preferably, the expression construct will be integrated into the genome of the selected expression host.

The present invention further provides vectors, preferably plasmids, for the cloning and/or transformation of microbial hosts via the introduction into the microbial host of the DNA constructs for the expression of the gene encoding the XYL B protein.

In addition, the present invention concerns homologous or heterologous hosts transformed by DNA constructs described above. Microbial expression hosts may be selected from bacteria, yeasts or fungi.

Within the context of the present invention, the term "homologous" is understood to intend all that which is native to the DNA sequence encoding the XYL B protein, including its regulatory regions. A homologous host is defined as the species from which such DNA sequence may be isolated.

The term "heterologous" is thus defined as all that which is not native to the DNA sequence encoding the XYL B protein itself, including regulatory regions. A "heterologous" host is defined as any microbial species other than that from which the XYL B-encoding gene has been isolated.

Within the scope of the present invention, a DNA sequence encoding a protein having the XYL B activity may be obtainable from an Aspergillus species, especially *Aspergillus niger*, *Aspergillus awamori*, *Aspergillus aculeatus*, and *Aspergillus tubigensis*. Most preferred is the xlnB gene originating from *Aspergillus tubigensis*, DNA sequences which hybridize under stringent conditions to the *Aspergillus tubigensis* xlnB gene and DNA sequences which encode a protein having XYL B activity, but where the codons are selected for optimal recognition in the chosen expression host.

According to the present invention, DNA sequences which hybridize under stringent conditions to the *Aspergillus tubigensis* xlnB gene are defined as hybridization conditions which are at least as stringent as the following hybridization protocol:

Pre-hybridization for 2 hrs at 60° C. in 6x SSC, 0.5% SDS, 5x Denhardt's solution, and 100 µg/ml heat denatured salmon sperm DNA. Hybridization for 18 hrs at 60° C. as described by Van den Broeck et al in European Patent Application 91205944.5 (publication no. 0 463 706 A2, Examples 2.1 and 7.1). After hybridization, the filters are washed twice in 4x SSC, 0.5% SDS, 0.1% sodium pyrophosphate, for 30 min at 60° C. and twice in 2x SSC, 0.1% SDS for 30 min at 60° C.

An endo-xylanase of interest may be identified via assay methods not critical to the present invention, such as a spot test assay. According to this method, a filtrate obtained from the culturing of a microorganism induced (e.g. with oat spelt xylan) to produce an endo-xylanase may be tested for the presence of endo-xylanase activity. Drops of the elution fractions are placed individually onto an agar film containing a citrate-phosphate buffer (see Example 1.1, below) and oat spelt xylan. The film is then incubated. If endo-xylanase activity is present, the location of the individual drops on the agar film are visibly clear.

Once a xylanase of interest has been identified, the DNA sequence encoding such xylanase may be obtained from the filamentous fungus which naturally produces it by culturing the fungus in a xylan-containing medium, isolating the desired xylanase using known methods such as column chromatography and determining at least a portion of the amino acid sequence of the purified protein.

According to the present invention, *Aspergillus tubigensis* was grown in a 3% oat spelt xylan medium to induce synthesis of xylanase mRNA. Poly $A^+$ mRNA cDNA was isolated using oligo(dT)-cellulose chromatography. From this poly $A^+$ mRNA, cDNA was synthesized using a ZAPT™-cDNA synthesis kit. About $3 \cdot 10^4$ recombinant phages were obtained after ligation of cDNA in vector arms and transforming *E. coli*. From this cDNA library, xlnB-specific clones were obtained by PCR technology. Oligonucleotides were derived from the N-terminal amino acid sequence and used in a PCR reaction in combination with poly $A^+$-specific oligonucleotides. A 0.7 kb DNA fragment was obtained which was the expected length based on the molecular weight of the XYL B protein. Using the 0.7 kb DNA fragment, a genomic library from *A. tubigensis* was screened. Six positive hybridizing plaques were obtained and analyzed by restriction enzyme digestion. A 5.5 kb HindIII genomic DNA fragment containing the xlnB gene was subcloned in the vector pEMBL18. The resulting plasmid was designated pIM170 and was deposited (in *E. coli*) on Dec. 14, 1992 at the Centraal Bureau voor Schimmelcultures in Baarn, the Netherlands and has been given accession number CBS 629.92.

To facilitate the insertion of the DNA fragment containing the xylanase-encoding sequence into expression constructs comprising one or more heterologous regulatory regions, the polymerase chain reaction (PCR) (Ehrlich, H. A. (editor), 1989) may be used for introduction of appropriate restriction enzyme sites in the 5' and 3' ends of the xylanase coding sequence. The choice of restriction sites depends on the DNA sequence of the expression vector, i.e. the presence of other restriction sites within the DNA molecule.

To obtain overexpression of the XYL B protein in the original (homologous) production species, or alternatively in another fungal strain, the complete XYL B-encoding gene including its 5' and 3' regulatory regions, or alternatively, the sequence encoding the mature XYL B protein fused to the regulatory regions of other genes, is introduced into the selected expression host to increase the copy number of the gene and, consequently, protein expression.

If a heterologous expression host is preferred, and a yeast or a bacterial strain is selected, an uninterrupted (intronless) DNA sequence is used for the construction of a heterologous expression vector in order to avoid the possibility that splice signals residing on the genomic fragment are not recognized by the heterologous host. This uninterrupted DNA sequence may be obtained from a cDNA library constructed from mRNA isolated from cells, induced for the synthesis of xylanases. This library may be screened with an oligonucleotide or cDNA probe obtained as described before. Alternatively, an uninterrupted DNA sequence may be obtained by applying a polymerase chain reaction using appropriate 5' and 3' oligonucleotides on the first strand cDNA synthesized from the RNA of xylan-induced cells.

Within the context of the present invention, overexpression is defined as the expression of the DNA sequence encoding the XYL B protein at levels above that which are ordinarily encountered in the homologous wild-type organism. In the same context, overexpression also intends the expression of the DNA sequence encoding the XYL B protein in a heterologous organism which does not normally produce the enzyme except for the introduction of the DNA sequence encoding the XYL B protein into the heterologous expression host. Progeny of these expression hosts are, of course, also to be understood to be embraced by the present invention.

Overexpression of the mature XYL B protein may also be achieved by the selection of heterologous regulatory regions, e.g promoter, secretion leader and terminator regions, which serve to increase expression and, if desired, secretion levels of the protein of interest from the chosen expression host and/or to provide for the inducible control of the expression of the gene.

Aside from the native promoter of the xlnB gene, other promoters may be used to direct its expression. The promoter may be selected for its efficiency in directing the expression of XYL B in the desired expression host.

In another embodiment, a constitutive promoter may be selected to direct the expression of XYL B, relatively free from other undesired enzyme activities. Such an expression construct is furthermore advantageous since it circumvents the need to culture the expression hosts on a medium containing solid xylans as an inducing substrate.

Examples of strong constitutive and/or inducible promoters which are preferred for use in fungal expression hosts are the ATP-synthetase, subunit 9 (oliC), triose phosphate isomerase (tpi), alcohol dehydrogenase (adhA), α-amylase (amy), amyloglucosidase (AG), acetamidase (amdS) and glyceraldehyde-3-phosphate dehydrogenase (gpd) promoters.

Examples of strong yeast promoters are the alcohol dehydrogenase, lactase, 3-phosphoglycerate kinase and triose-phosphate isomerase promoters.

Examples of strong bacterial promoters are the α-amylase and Spo2 promoters as well as promoters from extracellular protease genes.

Hybrid promoters may also advantageously be used to improve inducible regulation of the expression construct.

Preferred promoters according to the present invention are those originating from the amyloglucosidase (AG) gene and native xylanase promoters.

It is often desirable for the mature XYL B protein to be secreted from the expression host into the culture medium from where the enzyme may be more easily recovered.

According to the present invention, the secretion leader sequence native to the xlnB gene may be used to effect the secretion of the mature protein.

However, an increase in the expression of the xylanase sometimes results in the production of the protein in levels beyond that which the expression host is capable of processing and secreting, creating a build-up of protein product within the cell due to a bottleneck in the transport of the protein through the cell wall. Accordingly, the present invention also provides heterologous leader sequences to provide for the most efficient secretion of the xylanase from the chosen expression host.

According to the present invention, the secretion leader may be selected on the basis of the desired expression host. A heterologous secretion leader may be chosen which is homologous to the other regulatory regions of the expression construct. For example, the leader of the highly secreted amyloglucosidase protein may be used in combination with the amyloglucosidase promoter itself, as well as in combination with other promoters. Hybrid signal sequences may also advantageously be used within the context of the present invention.

Examples of preferred heterologous secretion leader sequences are those originating from the amyloglucosidase gene (fungi), the α-factor gene (yeasts) or the α-amylase gene (Bacillus).

Most preferred secretion leader sequences according to the present invention are the those originating from the amyloglucosidase (AG) gene and the native xylanase leader sequence.

In general, terminators are not considered to be critical elements for the overexpression of genes. If desired, a terminator may be selected from the same genes as the promoters, or alternatively, the homologous terminator may be employed.

In addition to the genomic fragment mentioned above, the transforming DNA may contain a selection marker to discriminate cells which have incorporated the desired gene from the bulk of untransformed cells. This selection marker, provided with the appropriate 5' and 3' regulatory sequences, may reside on the same DNA molecule containing the desired gene or be present on a separate molecule. In the latter case, a co-transformation must be performed. The ratio of the expression vector/selection vector must be adjusted in such a manner that a high percentage of the selected transformants also have incorporated the vector containing the XYL B-encoding expression construct.

The most suitable selection systems for industrial microorganisms are those formed by the group of selection markers which do not require a mutation in the host organism. Examples of fungal selection markers are the genes for acetamidase (amdS), ATP synthetase, subunit 9 (oliC) and benomyl resistance (benA). Exemplary of non-fungal selection markers are the G418 resistance gene (yeast), the ampicillin resistance gene (*E. coli*) and the neomycin resistance gene (Bacillus).

Once the desired expression construct has been assembled, it is transformed into a suitable cloning host such as *E. coli* to propagate the construct. Afterwards, the expression construct is introduced into a suitable expression host wherein the expression construct is preferably integrated into the genome. Certain hosts such as Bacillus species may be used as both cloning and expression hosts, thus avoiding an extra transformation step.

According to the present invention, a variety of expression hosts may be used to overexpress the XYL B protein. In one embodiment, a homologous expression host may be used. This involves the introduction of the desired expression construct back into the strain from which the XYL B-encoding DNA sequence was isolated either in increased gene copy numbers, or under the control of heterologous regulatory regions as described above, or both. In another embodiment, XYL B may be overexpressed by introducing and expressing the DNA construct encoding the mature XYL B protein under the control of the appropriate regulatory regions in heterologous hosts such as bacteria, yeasts or fungi. For that purpose, the DNA sequence encoding XYL B is preferably expressed under the control of promoter and terminator sequences originating from the heterologous host. In addition, it may be necessary to replace the secretion leader sequence native to the xlnB gene with a leader sequence homologous to the expression host in order to achieve the most efficient expression and secretion of the product.

The gram-negative bacterium *E. coli* is widely used as a host for heterologous gene expression, but mostly accumulates large amounts of heterologous protein inside the cell. Subsequent purification of the desired protein from the bulk of *E. coli* intracellular proteins can sometimes be difficult.

In contrast to *E. coli*, bacteria from the genus Bacillus are very suitable as heterologous hosts because of their capability to secrete proteins into the culture medium.

Alternatively, a heterologous host selected from the group of yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

A heterologous host may also be chosen to express XYL B which is substantially free from other polysaccharide-degrading enzymes by choosing a host which does not normally produce such enzymes such as *Kluyveromyces lactis*.

Examples of preferred expression hosts within the scope of the present invention are fungi such as Aspergillus species (described in EP 184.438 and EP 284.603) and Trichoderma species, bacteria such as Bacillus species (described in EP 134.048) and yeasts such as Kluyveromyces species (described in EP 96.430 and EP 301.670) and Saccharomyces species.

Particularly preferred expression hosts may be selected from *Aspergillus niger, Aspergillus awamori, Aspergillus aculeatus, Aspergillus Oryzae, Aspergillus tubigensis, Trichoderma reesei, Bacillus subtilis, Bacillus licheniformis, Kluyveromyces lactis* and *Saccharomyces cerevisiae*.

The overexpression of XYL B is effected by the culturing of the expression hosts, which have been transformed with the XYL B-encoding expression construct, in a conventional nutrient fermentation medium.

The fermentation medium consists of an ordinary culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer (e.g. oat spelt xylan) may be included.

The selection of the appropriate medium may be based on the choice of expression hosts and/or based on the regulatory requirements of the expression construct. Such media are well-known to those skilled in the art. The medium may, if desired, contain additional components favoring the transformed expression hosts over other potentially contaminating microorganisms.

The fermentation is performed over a period of 0.5–20 days in a batch or fed-batch process at a temperature in the range of between 0° and 45° C. and a pH between 2 and 10. Preferred fermentation conditions area at a temperature in the range of between 20 ° and 37 ° C. and a pH between 3 and 9. The appropriate conditions are selected based on the choice of the expression host.

After fermentation, the cells are removed from the fermentation broth by means of centrifugation or filtration. After removal of the cells, The XYL B protein may then be recovered and, if desired, purified and isolated by conventional means.

The product is stably formulated either in liquid or dry form. For certain applications, immobilization of the enzyme on a solid matrix may be preferred.

The XYL B enzyme, produced by means of the present invention, may be applied either alone, or together with other selected enzymes in a variety of processes requiring the action of a xylan-degrading enzyme.

The XYL B (or endoxylanase II) enzyme was used in two test systems, normally used in the paper and pulp industry. These are the Total Chlorine Free (TCF) and the Elementary Chlorine Free (ECF) systems. It was surprisingly shown that the XYL B enzyme especially increased the brightness of softwood pulp. The effect of this enzyme on hardwood was also found to be better than the effect of endoxylanase I and Lyx-68 (i.e. a mixture of endoxylanase I and endoxylanase II). Furthermore, the viscosity was not influenced dramatically.

The XYL B enzyme may thus advantageously be used to remove lignins from kraft pulp and thus facilitate bleaching by reducing the amount of chlorine needed in the preparation of paper products, especially in comparison to other Aspergillus xylanases such as the XYL A (endoxylanase I) enzyme due to the slightly higher temperature and pH optima of XYL B.

In accordance with the present invention, it has been found that the XYL B enzyme produced via the present invention may be used in the baking of breads to improve the quality of the dough or may also be added to animal feed compositions which are rich in arabinoxylans and glucoxylans. When added to feeds (including silage) for monogastric animals (e.g. poultry or swine) which contain cereals such as barley, wheat, maize, rye or oats or cereal by-products such as wheat bran or maize bran, the enzyme significantly improves the break-down of plant cell walls which leads to better utilization of the plant nutrients by the animal. As a consequence, growth rate and/or feed conversion are improved. Moreover, the XYL B protein may be used to the reduce the viscosity of feeds containing xylans.

The XYL B enzyme may be added beforehand to the feed or silage if pre-soaking or wet diets are preferred. More advantageously, however, the XYL B enzyme produced via the present invention when added to feed continue to hydrolyze xylans in the feed in vivo.

The XYL B enzyme produced via the present invention are also effective in improving filtration and removing dissolved organic substances from the broth in processes wherein apple distillery waste is bioconverted into microbial biomass.

Also according to the present invention, glucose syrups having improved filterability and/or lower viscosity are produced from impure cereal starch by subjecting the impure starch first to the action of an α-amylase, then to XYL B as produced via the present invention and finally to a hydrolysis. Similarly, XYL B may be used in beer brewing to improve the filterability of the wort.

In addition, the XYL B produced via the present invention may be used in other processes such as to increase yield in the preparation of fruit or vegetable juices, the enzymatic hydrolysis of sugar beet pulp, the resulting hydrolyzed fraction being capable of use in microorganism culture medium; of agricultural residues such as corn cobs, wheat-straw and ground nutshell; and of certain recyclable materials such as waste paper.

The following examples are provided so as to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Celsius and pressure is at or near atmospheric.

EXAMPLE 1

Partial Purification of Endo-Xylanase B (XYL B)

For the purification of endo-xylanases, *Aspergillus niger* DS16813, later reclassified as more likely belonging to the species *Aspergillus tubigensis* ((Kusters-van Someren et al. (1991), deposited at the Centraal Bureau voor Schimmelcultures, Baarn, The Netherlands on Jul. 20, 1990 and assigned the designation CBS 323.90) was grown and protein was purified as described in Example 1.1 of European Patent Application 91205944.5 (publication no. 0 463 706 A1), the disclosure of which is hereby incorporated in its entirety by reference.

Three endo-xylanases were purified XYL A in peak K, XYL B originally denoted as XYL 2 in peak F and XYL C in peak B.

EXAMPLE 2

Determination of the Amino Acid Sequence of XYL B

Approximately 1–2 nmol XYL B was subjected to electrophoresis on a 12.5% SDS-polyacrylamide gel, followed by electroblotting onto Immobilon-P membrane (Millipore), according to the method described by Matsudaira (1987). The membrane fragment containing the main band having an apparent molecular weight (SDS-page) of 22 kDa was subjected to sequence analysis in gas-phase sequencing (Amons, 1987) (SON facility, Leiden). The following sequence was determined:

(S)—T—P—S—S—T—G—E—N—(N)—G—F—Y—Y—(S)—(F)—(W?) (T)—(D) (SEQ ID NO:1)     (Formula 1)

This N-terminal sequencing was repeated once to verify the sequence obtained, then the following sequence was determined:

(G)/S—T/(G)—P/(G)—S—S—T—G/(T)—E—N—(N)—X—F—Y—Y—(S)—F—X—(T)—(D)—(G) (SEQ ID NO:2)     (Formula 2)

EXAMPLE 3

Molecular Cloning and Analysis of the XYL B-Encoding Gene xlnB

Example 3.1: Construction of the cDNA Expression Library

Example 3.1.1: Induction and Isolation of mRNA

*A. tubigensis* DS16813 was cultivated for 20, 28 and 44 hr. on minimal medium containing 3% oat spelt as a carbon source, after which mycelium was harvested by filtration and then washed with sterile saline. The mycelium was subsequently frozen in liquid nitrogen after which it was powdered using a Microdismembrator (Braun). Total RNA was isolated from mycelial powder in accordance with the guanidine monothiocyanate/LiCl protocol of Cathala et al. (1983), except that SDS was omitted from the solubilisation buffer. Poly A⁺ RNA was isolated from 1 mg of total RNA by oligo(dT)-cellulose chromatography (Aviv and Leder 1972, Sambrook et al. 1989) with the following modifications: 10 mM HEPES pH 7.6 was used as a buffer and SDS is omitted from all solutions, the loading buffer was supplemented with 9% (v/v) dimethylsulfoxide.

Example 3.1.2:

Construction of the cDNA library cDNA was synthesized from 5 µg poly A⁺ RNA and ligated into bacteriophage lambdaλ Uni-ZAP XR using the ZAP™-CDNA synthesis kit (Stratagene) according to the manufactures instructions. After ligation of the cDNA into Uni-ZAP XR vector-arms, the phage DNA was packaged using Packagene™ extracts (Promega). Ligation of 200 ng cDNA in 1 µg vector arms and subsequent packaging of one fifth of the reaction mixture resulted in a primary library consisting of $3 * 10^4$ recombinant phages. This primary library was amplified using E. coli PLK-F', titrated and stored at 4° C.

Example 3.2: Generation of cDNA Fragments By PCR

The N-terminal amino acid sequences as they were determined for XYL B were used to design oligonucleotide mixtures. From XYL B the following mixture was derived, 5' ACI GGI GAR AAY GGI TTY TA 3' (SEQ 10 No:3)

(Formula 3)

in which R stands for an A or a G; Y for a C or a T; I for inosine and N for A, G, C or T. This oligonucleotide was derived from the N-terminal amino acid sequence of XYL B from amino acid 6 (T) to amino acid 13 Y. The codon for the N at position 10 was omitted from this sequence due to its uncertainty.

This oligonucleotide mixture was used in PCR in combination with the oligonucleotide 5' GAG GAT CCG TCG ACT ACT GAC 3' (SEQ ID No:4) (Formula 4) using cDNA synthesized as described in Example 3.1 except that the first strand was primed using oligo 5' GAG GAT CCG TCG ACT ACT GAC TTT TTT TTT TTT TTT TTT 3' (Formula 5) (SEQ 10 No:5).

For a PCR 1 µl of the resulting cDNA was combined with 10 µl 10* reaction buffer (100 mM Tris-HCl , pH 8.3; 500 mM KCl; 15 mM MgCl₂; 0.01% gelatin), 16 µl 1.25 mM of each of the four deoxynucleotide triphosphates and 1 µg of each of the oligonucleotides in an end volume of 100 µl . The reaction mixture was mixed and 1 µl TAQ polymerase (5 U/ml)(HT BIOTECHNOLOGY) was added. The DNA was heat denatured by incubation for 3 min at 90° C. followed by 25 cycles of 1 min 90°, 1 min. 36° C. and 1 min 72° C. After these 25 cycles the mixture is incubated for 5 min. at 72° C.

Analysis of the reaction products revealed a fragment of about 0.7 kb using the oligo derived from XYL B (Formula 3). Based on an apparent molecular weight of 22 kDa for XYL B, a fragment of about 0.7 kb was expected.

Example 3.3

Screening of the A. niger var. tubigensis genomic Library for the XYL B Encoding gene xlnB Example 3.3.1:

Screening of the A. niger var. tubigensis genomic Library for the xlnB Gene

To screen the A. tubigenesis genomic library, constructed as described in Example 2 of European Patent Application 91205944.5 (publication no. 0 463 706 A1), for the xlnB gene $10^4$ pfu per plate were plated in NZYCM topagarose containing 0.7% agarose on 85-mm-diameter NZYCM (1.2% agar) plates as described (Maniatis et al., 1982, pp.64).

Plaque hybridisation using nitrocellulose filter (Schleiger & Schull) replicas was performed as follows; $10^4$ pfu were plated with E. coli LE392 cells in 0.6% topagarose. After overnight incubation of the plates at 37° C. two replicas of each plate were made on nitrocellulose filters as described by Maniatis et al., 1982 (pp. 320–321). The filters were wetted after which they were prehybridized at 68° C. for two h in prehybridization buffer containing; 6x SSC, 0.5% SDS, 5x Denhardt's solution ((100 * Denhardts solution contains per 500 ml: 10 g Ficoll-400; 10 g polyvinylpyrrolidone; 10 g Bovine Serum Albumin (Pentax Fraction V) (20x SSC per 1000 ml: 175.3 g NaCl, 107.1 g sodium citrate 5.5 H₂O, pH 7.0)) and 100 µg/ml heat denatured herring sperm DNA (Boehringer Mannheim). After two hours prehybridization the prehybridization buffer was replaced by hybridization buffer which was identical to the prehybridization buffer, except that this buffer contained the ³²P-labelled fragments obtained by PCR, isolated and labelled as described in European Patent Application 91205944.5 (publication no. 0 463 706 A1) (Examples 2.1.and 7.1). The filters were hybridized for 18 h at 68° C. After hybridization the filters were washed twice at 68° C. for 30 min in 5 * SSC/0.5% SDS, 0.1% sodium pyrophosphate followed by two washes during 30 min. at 68°C. in 2 * SSC/0.1% SDS. The air dried filters were taped on a sheet of Whatman 3MM paper, keying marks were made with radioactive ink and the Whatman paper and filters were covered with Saran Wrap. Hybridizing plaques were identified by exposure of Kodak XAR X-ray film for 4 h at room temperature.

Hybridizing plaques, appearing in duplicate on the replica filters, were identified; six positive plaques were picked. Each positive plaque was picked from the plate using a Pasteur pipette and the phages were eluted from the agar plug in 1 ml of SM buffer (SM buffer per 1000 ml: 5.8 g NaCl, 2.0 g MgSO₄·7H₂O, 50 ml 1M Tris/HCl pH 7.5, 5 ml 20% gelatin) containing 20 µl chloroform, as described in Maniatis et al. (1982, pp. 64). The phages obtained were purified by repeating the procedure described above using filter replicas from plates containing 50–100 plaques of the isolated phages.

After purification the phages were propagated by plating 5x 10³phages on NZYCM medium (NZYCM medium per 1000 ml: 10 g NZ amine, 5 g NaCl, 5 g yeast extract, 1 g casamino acids, 2 g MgSO₄·7H2O pH 7.5; for plates 12 g agar is added, for topagarose 7 g agarose). After overnight incubation at 37° confluent plates were obtained, from which the phages were eluted by adding 5 ml SM buffer and storing the plates for 2 hrs. at 4° C. with intermittent shaking. After collection of the supernatant using a pipette, the bacteria were removed from the solution by centrifugation at 4,000x g for 10 min. at 4° C. To the supernatant 0.3% chloroform was added and the number of pfu is determined by titration as described in Example 2.4 of European Patent Application 91205944.5 (publication no. 0 463 706 A1). These phage stocks contain approximately $10^{10}$ pfu/ml.

Example 3.3.2:

Restriction Analysis of xlnB Containing Phages

The DNA of the positive phages isolated as described in Example 3.3 of European Patent Application 91205944.5 (publication no. 0 463 706 A1), was analyzed by Southern analysis. The DNA was digested for 3 h. at 37° C. in a reaction mixture composed of the following solutions; 5 µl (≈1 µg) DNA solution; 2 µl of the appropriate 10x React buffer (BRL); 10 U restriction enzyme (BRL) and sterile distilled water to give a final volume of 50 µl . After digestion the DNA was precipitated by the addition of 0.1 vol. 3M NaAc and 2 vol. ethanol. The DNA was collected by centrifugation for 10 min. at room temperature (14,000= g). The supernatant was removed by aspiration, the remaining pellet was briefly dried under vacuum and resuspended in 20 μl sterile distilled water. After addition of 4 μl DNA loading buffer (0.25% (w/v) bromophenolblue, 0.25% (w/v) xylene cyanol, 15% (w/v) Ficoll type 400 in $H_2O$) the samples were incubated for 10 min. at 65° C. and rapidly cooled on ice, before loading the samples on a 0.6% agarose gel in TAE buffer (50x TAE buffer per 1000 ml: 242.0 g Trizma base (Sigma), 57.1 ml glacial acetic acid, 100 ml 0,5 M EDTA pH 8.0). The DNA fragments were separated by electrophoresis at 25 V for 15–18 h.

After electrophoresis the DNA was transferred and denatured by alkaline vacuum blotting (VacuGene XL, Pharmacia LKB) to nylon membrane (Gene Bind 45, Pharmacia LKB) as described in the instruction manual (pp. 25–26) and subsequently prehybridized and hybridized using $^{32}P$ labeled fragment and hybridization conditions as described in Example 3.3.1. The hybridization pattern was obtained by exposure of Kodak XAR-5 X-ray film for 2 h. at room temperature.

The restriction patterns obtained were used to derive a partial restriction map of the genomic region of the xlnB gene.

Example 3.3.3:

Sub cloning of the *A. tubigensis* xlnB Gene

For xlnB a 5.5 kb HinDIII fragment was selected to subclone to identify the selected gene in expression. The fragment was isolated by digesting the phage DNA and subsequent agarose electrophoresis. The fragment was cut from the agarose gel, after which it was recovered from the piece of agarose by electroelution using ISCO cups as described in Example 3.5 of European Patent Application 91205944.5 (publication no. 0 463 706 A1).

The fragment obtained was ligated in the vector pEMBL18 digested with HinDIII prepared as follows; 1 μl (1 μg/μl) pEMBL18 was mixed with 2 μl 10x React 2 (BRL), 1 μl (10 U/μl) NsiI, 1 μl (10 U/μl) XbaI and 16 μl sterile distilled water. The DNA is digested for 1 h at 37° C. The vector was isolated from a 0.6% agarose gel as described above.

The 5.5 kb HindIII fragment was ligated in the vector resulting in the plasmid pIM170 by the following procedure: 100 ng pEMBL18 fragment was mixed with 100 ng 5.5 kb HindIII/XbaI fragment and 4 μl 5 * ligation buffer (composition; 500 mM Tris-HCl, pH 7.6; 100 mM $MgCl_2$; 10 mM ATP; 10 mM dithiotreitol; 25% PEG-6000) and 1 μl (1.2 U/μl) $T_4$ DNA ligase (BRL) was added to this mixture to give a final volume of 20 μl . After incubation for 16 h at 14°C. the mixture was diluted to 100 μl with sterile water. 10 μl of the diluted mixture was used to transform *E. coli* DH5α competent cells prepared as follows: 200 μl of an *E. coli* DHα overnight culture pregrown in LB medium was used to inoculate 200 ml of LB medium (LB medium per 1000 ml: 10 g trypticase peptone (BBL), 5 g yeast extract (BBL), 10 g NaCl, 0.5 mM Tris-HCl pH 7,5). This culture was incubated in an orbital shaker at 37° C. until its density corresponded to an $O.D._{600}$ of 0.15–0.2. The bacteria were then collected by centrifugation at 5000 rpm at 4° C. After discarding the supernatant the cells were kept on ice constantly. The bacterial pellet was washed in 100 ml 100 mM $MgCl_2$, 5 mM Tris-HCl pH 7.4 by resuspending these cells followed by centrifugation as described above. This was repeated with 100 ml 100 mM $CaCl_2$, 5 mM Tris-HCl pH 7.4. Finally the cells were resuspended in 2 ml 100 mM $CaCl_2$, 5 mM Tris-HCl pH 7.4, 14% glycerol. Aliquots (50 μl ) were either used immediately for transformation or frozen at −70° C.

*E. coli* DH5α competent cells were used in transformation experiments by combining 50 μl of the cells suspension with 10 μl of the ligation mixture. After a 30 min incubation period on ice, the cells were incubated for 3–5 min at 42° C. Then 1 ml LB medium was added and the cells were incubated at 37° C. for 1 h. Cells were concentrated by brief centrifugation and resuspending the cells in 200 μl LB medium. The resulting bacterial suspension was plated on LB medium containing 200 μg/ml ampicillin, 50 μg/ml X-gal and 60 μg/ml IPTG.

A selection of six of the resulting colonies was grown overnight in LB medium containing 200 μg/ml ampicillin. From the cultures plasmid DNA was isolated by the alkaline lysis method as described by Maniatis et al. (1982, pp. 368–369), which is used in restriction analysis to select a clone harbouring the desired plasmid pIM170. Plasmid DNA was isolated on a large scale from 500 ml cultures *E. coli* DH5α containing pIM170 grown in LB medium containing 100 μg/ml ampicillin (Maniatis et al., 1982, p.86). The plasmid was purified by CsCl centrifugation, phenolyzed, ethanol precipitated and dissolved in 400 μl TE (TE solution=10 mM Tris/HCl pH 8.0, 1 mM EDTA). The yield was approximately 500 μg.

Figure 1:
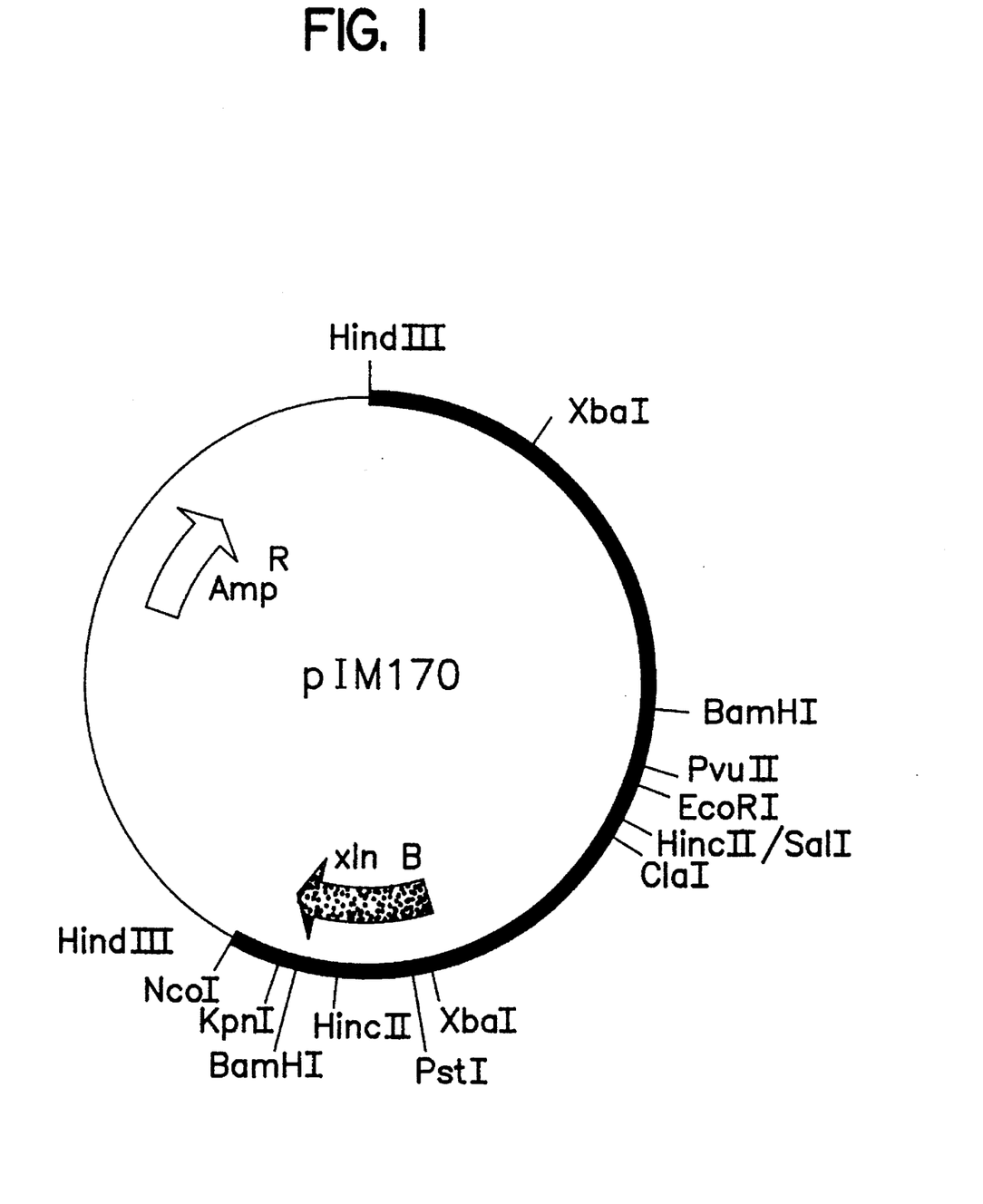
FIG. 1 Partial restriction map of pIM170. The bold line represents the HinDIII fragment subcloned in pEMBL18. The position and the orientation of the xlnB gene are indicated.

The plasmid pIM170 was further analyzed using restriction enzymes resulting in a partial restriction map as shown in FIG. 1.

*E. coli* DH5α containing pIM170 has been deposited on Dec. 14, 1992 at the Centraal Bureau voor Schimmelcultures in Baarn, the Netherlands and has been given accession number CBS 629.92.

Example 3.4: The Primary Structure of the xlnB Gene
Example 3.4.1:

Sequence analysis of the *A. tubigensis* xlnB Gene

The primary structure of the *A. tubigensis* xlnB gene, part of the promoter/regulation region, the coding part of the gene and the termination region, was determined by sequencing fragments of the 5.5 kb HinDIII from pIM170, combined with the use of specific oligonucleotides as primers in the sequencing reactions.

For nucleotide sequence analysis restriction fragments were isolated as described in Example 2.2.4 and were then cloned in pEMBL18/19 vectors (Dente et. al., 1983) digested with the appropriate restriction enzymes. The nucleotide sequences were determined by the dideoxynucleotide chain-termination procedure (Sanger et al., 1977) using the Pharmacia T7 DNA polymerase sequencing kit. Computer analysis is done using the PC/GENE program.

Figure 2:
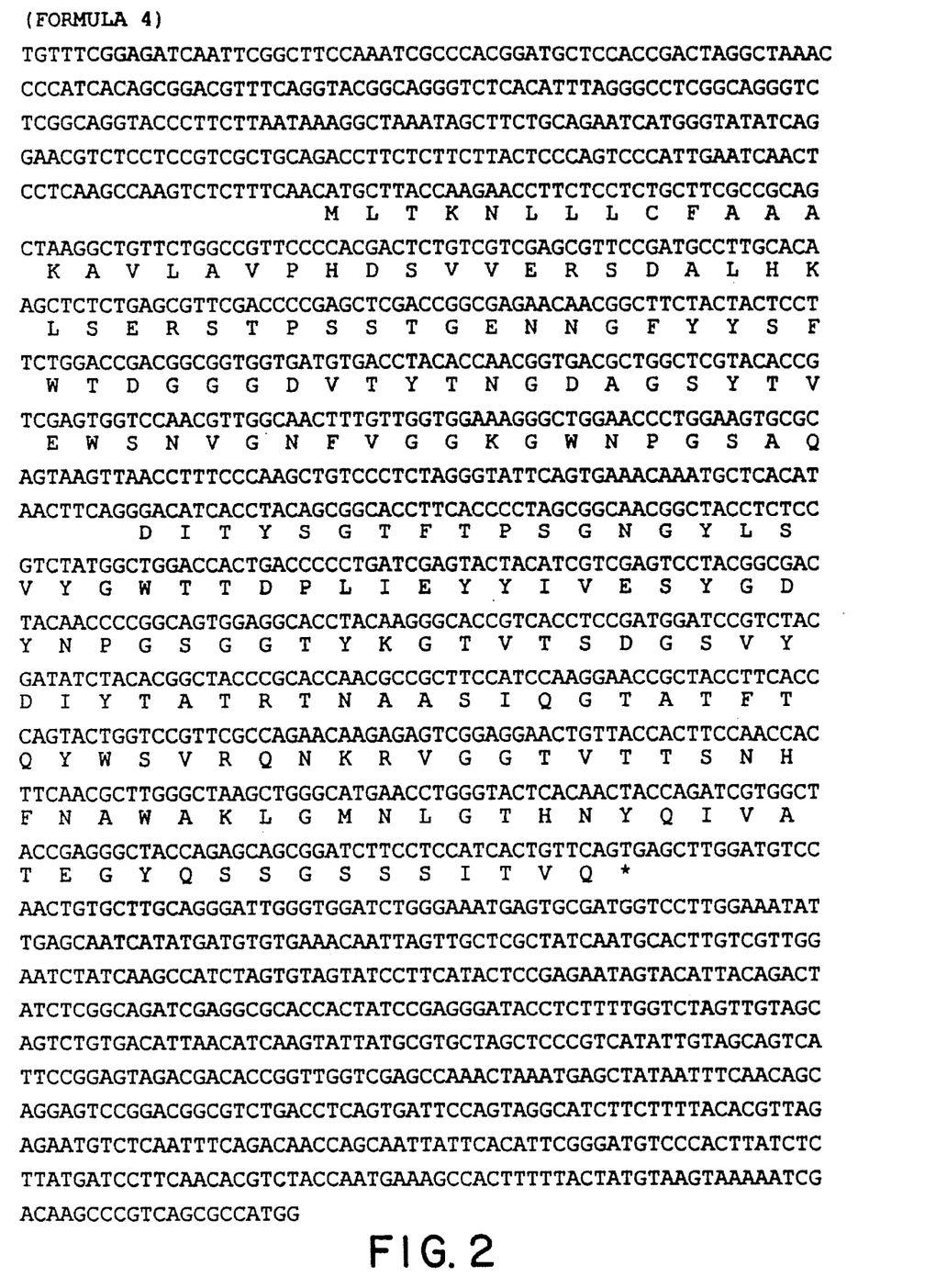
FIG. 2 (SEQ ID No:7 and SEQ ID No:8): (Nucleotides 638-2219 of SEQ ID NO:7). Nucleotide sequence of the *A. tubigensis* xlnB gene and the amino acid sequence derived therefrom. The N-terminal amino acid sequence as was determined from the enzyme is found from position 124 through position 180 in the nucleotide sequence in frame 1. In this sequence one putative intron is recognized which is located at position 290 through 357, indicated ( ).

The complete nucleotide sequence has been determined and is given in FIG. 2 (Formula 4, SEQ ID No: 7).

Example 3.4.2:

Description of the xln B Gene

The sequence obtained comprises 1581 bp, 263 bp in the 5' non-coding region and 576 bp in the 3' non-coding region. In the 5' upstream region putative TATA-boxes are found at positions 138 till 145 and 173 till 177. At position 100 till 106 a seven bp. element is found, which is part of a triplicate repeated sequence found in the primary structure of the *A. tubigensis* xlnA gene (European Patent Application 91205944.5 (publication no. 0 463 706 A1), Example 4.2). At position 86 till 97 a 12 bp sequence (CGGCAGGGTCTC(SEQ ID No:6), Formula 6) is found, which is repeated from position 111 till position 122.

The coding part of xlnB gene is 742 bp long and is interrupted by a single putative intron 67 bp long. The polypeptide derived from the coding sequence is 225 amino acids long. The N-terminal sequence determined as described in Example 2.2 is preceded by a 37 amino acid prepro peptide. The mature protein is 188 amino acids in size and has a predicted molecular weight of 20 kDa and a theoretical IEP of 4.3.

EXAMPLE 4

Expression of the Cloned xlnB Gene in *A. niger*

The plasmid pIM170 was introduced in *A. niger* by cotransformation of *A. niger* N593 using the *A. niger* pyrA gene, located on the plasmid pGW635 (Goosen et al., 1987), as a selective marker and the plasmid pIM170 as the cotransforming plasmid.

Protoplasts were prepared from mycelium obtained after growth on minimal medium supplemented with 0.5% yeast extract, 0.2% casamino acids, 50 mM glucose and 10 mM uridine for 20 h at 30° C. The preparation of protoplasts of and the transformation procedure was performed as described by Goosen et al., (1987), using 1 µg pGW635 and 50 µg pIM170. (minimal medium per 1000 ml: 6.0 g $NaNO_3$, 1.5 g $KH_2PO_4$, 0.5 g $MgSO_4·7H_2O$, 0.5 g KCl 1 ml Visniac solution, Carbon source as indicated, pH 6.0; Visniac solution (Visniac and Santer, 1957): 10 g EDTA, 4.4 g $ZnSO_4·7H_2O$, 1.0 g $MnCl_2·4H_2O$, 0.32 g $CoCl_2·6H_2O$, 0.32 g $CuSO_4·5H_2O$, 0.22 g $(NH_4)_6Mo_7O_{24}·4H_2O$, 1.47 g $CaCl_2·2H_2O$, 1.0 g $FeSO_4·7H_2O$, pH 4.0)

The $PYR^+$ to transformants obtained were then analyzed for the expression of the xlnB gene by analysis of culture filtrates after 30 h growth of the transformants on minimal medium containing 3% oat spelt xylan as a carbon source by SDS-PAGE. Total protein in the culture filtrate was analyzed by SDS-PAGE and detected by Coomassie Brilliant blue, while the XYL B was visualized using antibodies raised against partial purified XYL B after Western blotting as described in European Patent Application 91205944.5 (publication no. 0 463 706 A1).

Analysis of filtrate and Coomassie Brilliant blue staining revealed a clear overexpression of the xln B gene in a number of transformants analyzed. In these transformants a protein is found having an apparent molecular weight corresponding to the XYL B protein and which is produced in strongly increased levels compared to the wild-type *A. niger* strain N402. Transformant N593:170-2 produces the highest level of XYL B, while the transformants N593: 170–7; 8; 9; 10 and 11 also strongly increased levels are produced.

EXAMPLE 5

Delignification of Oxygen Predelignified Kraft Pulp With Xylanases in a TCF and in An ECF Sequence Properties of the pulp used in this experiment:

|  | Hardwood Birch 80% | Softwood spruce, 20% pine |
|---|---|---|
| Brightness, % ISO | 50.8 | 35.8 |
| Kappa number | 11.0 | 16.7 |
| Viscosity, $dm^3/kg$ | 979 | 1003 |
| Calcium, ppm | 1900 | 2600 |
| Copper, ppm | 0.3 | 0.6 |
| Iron, ppm | 5.1 | 11 |
| Magnesium, ppm | 210 | 270 |
| Manganese, ppm | 25 | 70 |

Three enzyme preparations from *A. niger*, xylanase Endo I (European patent application EP 463706), xylanase Endo II (=Xylanase B) and Lyx 68, a commercially available preparation containing both xylanases Endo I and Endo II, have been tested in a Totally Chlorine Free (TCF) bleaching sequence represented by $X_wQP$, indicating the following steps:

enzyme incubation (X), washing (W), chelating (Q) and peroxide bleaching (P).

As parameters for measuring the performance brightness, kappa reduction and viscosity were measured. Brightness is an important measure because paper is more valuable if it is 'whiter'. Kappa reduction is a measure for the release of certain compounds and not necessarily related with brightness. The viscosity of the pulp is a measure for the strength of the paper obtainable from the pulp.

It should be noted that the sequence QP forming part of the above bleaching sequence has been described previously in European patent application EP 402 235 (in the name of Eka Nobel).

The following incubations were performed:

| Enzyme step, X | Temperature, °C. | 50 |
|---|---|---|
|  | Time, minutes | 120 |
|  | Consistency, % | 10 |
|  | pH | 4 ± 0.5 (Endo I) |
|  |  | 5 ± 0.5 (Endo II) |
|  |  | 4.5 ± 0.5 (Lyx 68) |
|  | Dosage, units/g pulp | 50 |
| Washing step, W | Temperature, °C. | ambient |
|  | Time, minutes | 10 |
|  | Consistency, % | 3.5 |
|  | pH | "as is" and alkaline (7–11) |
| Q stage, | Temperature, °C. | 90 |
|  | Time, minutes | 60 |
|  | Consistency, % | 10 |
|  | pH | 5–7 |
|  | Dosage, kg EDTA/ton pulp | 2 |
| P step, | Temperature, °C. | 90 |
|  | Time, minutes | 240 |
|  | Consistency, % | 10 |
|  | pH | 10.6–11.8 |
|  | Dosage, kg EDTA/ton pulp | 25 |

Experiments were performed on softwood and hardwood. In the blank the equivalent procedure was followed without addition of enzyme. After the procedure pulp viscosity was measured and handsheets were produced and kappa reduction, brightness and viscosity were measured. The following results were obtained:

|  | % ISO brightness | kappa-reduction | viscosity |
|---|---|---|---|
| HARDWOOD: |  |  |  |
| Blank | 81.1 | 38 | 891 |
| Endo I | 83.3 | 50 | 968 |
| Endo II | 83.9 | 43 | 891 |
| Lyx 68 | 82.2 | 48 | 885 |
| SOFTWOOD: |  |  |  |
| Blank | 71.7 | 55 | 900 |
| Endo I | 73.0 | 59 | 914 |
| Endo II | 75.7 | 61 | 859 |
| Lyx 68 | 74.6 | 62 | 888 |

The results shown above indicate that the use Endo II in the TCF process leads to a considerable increase in brightness both when hardwood and softwood pulp is used. The effect is larger on softwood 4.0% than on hardwood 2.8%. Furthermore the effect is larger than when Endo I or Lyx-68 are employed.

Additionally, to test Endo II (+ XYL B) in an Elementary Chlorine Free (ECF) bleaching sequence, a $XD_{100}ED$ bleaching sequence was applied indicating the enzyme incubation (X); the chlorine dioxide (D) and the alkaline extraction (E) stages. Lyx-68 containing both Endo I and Endo II was added and incubated under conditions (pH 5.5) in which only Endo II shows relevant activity. The residual activity of Endo I at pH 5.5 is less than 10%. After the above bleaching sequence, brightness was measured and compared to a bleaching sequence in which enzyme was omitted. The following enzyme concentrations were used: 0; 100; 175; 250; 400; 550; 1100 U/g pulp.

The pulp used had a Kappa number of 22.4 and a viscosity of 21.2 mPa.s.

The following protocol was used:

| Enzyme step, X | Temperature, °C. | 51 |
| | Time, minutes | 120 |
| | Consistency, % | 10 |
| | pH | 5.0 |
| Washing step, W | Temperature, °C. | ambient |
| | Time, minutes | 10 |
| | Consistency, % | 3.5 |
| | pH | 10 |
| $D_{100}$ stage | Temperature, °C. | 50 |
| | Time, minutes | 40 |
| | Consistency, % | 3.5 |
| | pH (final) | 2.2 |
| | Dosage, $ClO_2$% on pulp | 1.87 |
| E stage | Temperature, °C. | 70 |
| | Time, minutes | 60 |
| | Consistency, % | 10 |
| | pH | 10.6–11.8 |
| | Dosage, NaOH (% on pulp) | 0.8 |
| D stage | Temperature, °C. | 70 |
| | Time, minutes | 180 |
| | Consistency, % | 10 |
| | pH (final) | 3.7 |
| | Dosage, $ClO_2$% on pulp | 2.0 |

The following results were obtained:

| Enzyme added (U/g pulp) | Brightness (% ISO) after $XD_{100}ED$ |
|---|---|
| 0 | 80.1 |
| 100 | 83.1 |
| 175 | 83.5 |
| 250 | 84.0 |
| 400 | 84.0 |
| 550 | 83.6 |
| 1100 | 84.7 |

Again it can be concluded that Endo II has a considerable effect on the brightness of pulp. Optimal dosage is in the range of 175–550 U/g pulp.

References

Anons, R. (1987) FEBS Lett., 212, 68–72.
Aviv, H. and Leder, P. (1972) Proc. Natl. Acad. Sci. USA, 69, 1408–1412.
Biely, P., Mislovicova, D. and Toman, R. (1985a) Anal. Biochem, 144, 142–146.
Biely, p., Markovic, O. and Mislovicova, D. (1985b) Anal. Biochem., 44, 147–151.
Boel, E. et al. (1984a) EMBO J., 3, 1097–1102.
Boel, E. et al. (1984b) Mol. Cell. Biol., 4, 2306–2315.
Carré, B. and Brillouet, J. M. (1986) J. Science and Food Agric., 37, 341–351.
Cathala, G., Savouret, J-F., Mendez, B., West, B. L., Karin, M., Martial, J. A., Baxter, J. D. (1983) DNA, 2, 329–335.
Chesson, A. (1987) *Recent Advance in Animal Food Nutrition*, Haresign, W. and Cole, D. J. A., eds:, Butterworth, London, 71–89.
Cove, D. (1966) Biochem. Biophys. Acta, 113, 51–56.
Dekker, R. F. A. and Richards, G.M. (1977) Adv. Carb. Chem. and Biochem., 32, 278–353.
Ehrlich, H. A., ed. (1989) *PCR Technology: Principles and Applications for DNA Amplification*, Stockton Press, New York.
Goosen, T., Bloemheuvel, G., Gysler, C., de Bie, D. A., van den Broek, H. W. J. and Swart, K. (1987) Curr. Genet., 11, 499–503.
Goosen, T., van Engelenburg, F., Debets, F., Swart, K., Bos, K. and van den Broek, H. W. J. (1989) Mol. Gen. Genet., 219, 282–288.
de Graaff, L. H., van den Broek, H. W. J. and Visser, J. (1988) Curr. Genet., 13, 315–321.
Gurr, S. J., Unkles, S. E. and Kinghorn J. R. (1987) In: *Gene Structure in Eukaryotic Microbes*, vol. 22, Kinghorn, J. R., ed., IRL Press, Oxford, 93–139.
Hanahan, D. (1983) J. Mol. Biol., 166, 557.
Kelly, J. and Hynes, M. (1985) EMBO J. 4, 475–479.
Kormelink, F. J. M. (1992) Doctoral Thesis, Agricultural University, Wageningen, the Netherlands.
Kusters-van Someren, M. A., Samson, R. A. and Visser, J. (1991) Curr. Genet., 19, 21.
Laemmli, U. K. (1970) Nature, 227, 680–685.
Leathers, T. D., Kurtzman, C. P., Detroy, R. W. (1984) Biotechnol. Bioeng. Symp., 14, 225.
Maniatis, T., Fritsch, E. F., Sambrook, J. (1982) *Molecular Cloning, A Laboratory Manual*, Cold Spring Harbor Laboratory, New York.
Matsudaira, P. (1987) J. Biol. Chem., 262, 10035–10038.
McCleary, B. V. and Matheson, N. K. (1986) Adv. Carb. Chem. and Biochem., 44, 147–276.
Messing, J. (1983) Methods in Enzymology, 101C, 20–78.
Moonen, J. H. E., Scheepstra, A., Graveland, A. (1982) Euphitica, 31, 677.
Murray, N. (1977) Mol. Gen. Genet., 150, 53–58.
Norrander, J., Kempe, T. and Messing, J. (1983) Gene, 26, 101–106.
Poutanen, K. and Puls, J. (1988) Appl. Microbiol. Biotechnol., 28, 425.
Saiki, R. K. et al. (1988) Science, 239, 487–491.
Sambrook, J., Fritsch, E. F., Maniatis, T. (1989) In: *Molecular Cloning: a Laboratory Manual,* 2nd edn., Cold Spring Harbor Laboratory Press, N.Y.
Sanger, F., Nickelen, S. and Coulson, A. R. (1977) Proc. Natl. Acad. Sci. USA, 74, 5463–5467.
Tilburn, J. t al. (1983) Gene, 26, 205–221.
Van den Broeck, H. C. et al. (1992) European Patent Application 91205944.5, publication no. 0 463 706 A1.
Vieirra, J. and Messing, J. (1982) Gene, 19, 259–268.
Visniac, W. and Santer, M. (1957) Bact. Rev., 21, 195–213.
Wernars, K. (1986) Thesis, Agricultural University, Wageningen, the Netherlands.
Wong, K. K. Y., eta. 1. (1988) Microbiol. Rev., 52, 305–317.
Woodward, G. (1984) Topics in Enzyme Ferment. Biotechnol., 8, 9–30.
Yanisch-Perron, C., Viera, J. and Messing, J. (1985) Gene, 33, 103–109.

We claim:

1. A purified and isolated polynucleotide molecule which encodes a polypeptide having the xylanase activity of the *Aspergillus tubigensis* xylanase B enzyme wherein the nucleotide sequence of said polynucleotide molecule is selected from the group consisting of:

a) the nucleotide sequence of FIG. 2 or SEQ ID NO:7;

b) nucleotide sequences encoding the xylanase B polypeptide of 225 amino acids shown in FIG. 2 or SEQ ID NO:8; and c) nucleotide sequences encoding the mature xylanase B polypeptide of 188 amino acids shown at amino acid positions 38–225 in FIG. 2 or SEQ ID NO:8.

2. An expression construct which comprises a polynucleotide molecule according to claim 1, wherein said polynucleotide molecule is operably linked to regulatory regions which direct expression of the encoded polypeptide having xylanase B activity in a suitable expression host.

3. The expression construct of claim 2, in which said regulatory regions further comprise one or more of the following components: a promoter selected from the group consisting of the promoter originating from an amyloglucosidase gene and the promoter native to a xylanase gene; and a secretion leader sequence selected from the group consisting of the secretion leader sequence originating from an amyloglucosidase gene and the secretion leader sequence native to a xylanase gene.

4. A transformed microbial host cell wherein said microbial host contains the expression construct according to claim 2 and expresses the encoded xylanase B enzyme.

5. The transformed microbial host of claim 4 which is selected from the genera consisting of Aspergillus, Kluyveromyces, Trichoderma, Saccharomyces and Bacillus.

6. A method for expression of a polypeptide having the xylanase activity of the *Aspergillus tubigensis* xylanase B enzyme wherein the method comprises the steps of:

a) culturing a transformed microbial host according to claim 4 under conditions conducive to the expression of said polypeptide having xylanase B activity; and b) recovering said polypeptide.

7. The plasmid pIM170 which has the accession number CBS-629.92 at the Centraalbureau voor Schimmelcultures (CBS).

8. Purified and isolated expression and transcription regulatory regions as found in the 5' non-coding sequence of the *Aspergillus tubigensis* xln B gene shown as nucleotides 100–263 in FIG. 2 (nucleotides 738–901 of SEQ ID NO:7).

9. A purified and isolated polynucleotide molecule which hybridizes under stringent conditions to the DNA molecule of FIG. 2 or SEQ ID NO:7.

10. A polynucleotide molecule according to claim 9 wherein said molecule is obtained from a filamentous fungus.

11. A polynucleotide molecule according to claim 10 wherein said fungus belongs to the genus Aspergillus.

12. A polynucleotide molecule according to claim 11 wherein said filamentous fungus is a strain of *Aspergillus tubigensis*.

13. A recombinant polynucleotide molecule comprising a polynucleotide molecule according to claim 9 and a vector.

14. A recombinant polynucleotide molecule comprising a regulatory region according to claim 8 and a vector.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
      ( A ) LENGTH: 19 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: N-terminal ( v i i ) IMMEDIATE SOURCE:
      ( B ) CLONE: formula 1

( i x ) FEATURE:
      ( A ) NAME/KEY: Peptide
      ( B ) LOCATION: one-of(1, 10, 15, 16, 17, 18, 19)
      ( D ) OTHER INFORMATION: /label= X
            / note= "X has the following most probable
            assignments: 1=Ser, 10=Asn, 15=Ser, 16=Phe,
            17=Trp, 18=Thr, 19=Asp"

( x i ) SEQUENCE DESCRIPTION: SEQ ID NO: 1:

Xaa  Thr  Pro  Ser  Ser  Thr  Gly  Glu  Asn  Xaa  Gly  Phe  Tyr  Tyr  Xaa  Xaa
    1                   5                        10                        15

Xaa  Xaa  Xaa ( 2 ) INFORMATION FOR SEQ ID NO: 2:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( v ) FRAGMENT TYPE: N-terminal ( v i i ) IMMEDIATE SOURCE:
      ( B ) CLONE: formula 2

( i x ) FEATURE:
      ( A ) NAME/KEY: Peptide
      ( B ) LOCATION: one-of(1, 2, 3, 7, 10, 15, 18, 19, 20)
      ( D ) OTHER INFORMATION: /label= X
            / note= "Alternative assignments for positions
            1:Gly, 2:Gly, 3:Gly, 7:Thr. Probable assignments
            for X: 10=Asn, 15=Ser, 18=Thr, 19=Asp, 20=Gly"

( x i ) SEQUENCE DESCRIPTION: SEQ ID NO: 2:

Ser  Thr  Pro  Ser  Ser  Thr  Gly  Glu  Asn  Xaa  Xaa  Phe  Tyr  Tyr  Xaa  Phe
    1                   5                        10                        15

Xaa  Xaa  Xaa  Xaa
                   20

( 2 ) INFORMATION FOR SEQ ID NO: 3:

( i ) SEQUENCE CHARACTERISTICS:
      ( A ) LENGTH: 20 base pairs
      ( B ) TYPE: nucleic acid

```
            ( C ) STRANDEDNESS: single
            ( D ) TOPOLOGY: linear ( i i ) MOLECULE TYPE: DNA (genomic)

( i i i ) HYPOTHETICAL: NO ( v i i ) IMMEDIATE SOURCE:
            ( B ) CLONE: formula 3

( i x ) FEATURE:
            ( A ) NAME/KEY: misc_feature
            ( B ) LOCATION: one-of(3, 6, 15)
            ( D ) OTHER INFORMATION: /label= N
                    / note= "N at position 3, 6, and 15 is inosine"

( x i ) SEQUENCE DESCRIPTION: SEQ ID NO: 3:

ACNGGNGARA  AYGGNTTYTA                                                                  20

( 2 ) INFORMATION FOR SEQ ID NO: 4:

( i ) SEQUENCE CHARACTERISTICS:
                ( A ) LENGTH: 21 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( v i i ) IMMEDIATE SOURCE:
                ( B ) CLONE: formula 4

( x i ) SEQUENCE DESCRIPTION: SEQ ID NO: 4:

GAGGATCCGT  CGACTACTGA  C                                                               21

( 2 ) INFORMATION FOR SEQ ID NO: 5:

( i ) SEQUENCE CHARACTERISTICS:
                ( A ) LENGTH: 39 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( v i i ) IMMEDIATE SOURCE:
                ( B ) CLONE: formula 5

( x i ) SEQUENCE DESCRIPTION: SEQ ID NO: 5:

GAGGATCCGT  CGACTACTGA  CTTTTTTTTT  TTTTTTTT                                            39

( 2 ) INFORMATION FOR SEQ ID NO: 6:

( i ) SEQUENCE CHARACTERISTICS:
                ( A ) LENGTH: 12 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( v i i ) IMMEDIATE SOURCE:
                ( B ) CLONE: formula 6

( x i ) SEQUENCE DESCRIPTION: SEQ ID NO: 6:

CGGCAGGGTC  TC                                                                          12
```

5,610,046

23

24

-continued ( 2 ) INFORMATION FOR SEQ ID NO: 7:

( i ) SEQUENCE CHARACTERISTICS:
        ( A ) LENGTH: 2219 base pairs
        ( B ) TYPE: nucleic acid
        ( C ) STRANDEDNESS: double
        ( D ) TOPOLOGY: linear     ( i i ) MOLECULE TYPE: DNA (genomic)

( i i i ) HYPOTHETICAL: NO

( v i ) ORIGINAL SOURCE:
        ( A ) ORGANISM: Aspergillus tubigensis
        ( B ) STRAIN: DS16813

( i x ) FEATURE:
        ( A ) NAME/KEY: CDS
        ( B ) LOCATION: join(902..1180, 1248..1643)

( x i ) SEQUENCE DESCRIPTION: SEQ ID NO:7:

```
CACTATTGGC  GCCCCACCCA  GTGGAGACTT  ATACTACAAG  GTATCGGGCG  GCTATCTGAG    60

CAATCGGATC  TTCTTAAGCC  ACAGGCTAAT  ATCAAACAC   TTGTGGCGTC  TAGCCTTGTT   120

TTTATTTGAC  CGTCGGGAAG  CCGGTTCTGC  ACAACCTTTT  CCCTCGCGTT  CTACTTTCCA   180

ATTAGGTTTC  ATGCGAAGGA  TCTCAATTGG  CACCTTCCTT  AATAAGTAGT  GATAGTATTA   240

TCCTCAAATT  TAACGCGGCG  GTGGCACTCT  GCTAAGTCAC  TAACGGCAGG  AGACACTCCC   300

TCAAGTTAGC  ACACGCTAGC  ATTTTCTTTC  TTAACTAGGT  AGAAGCAGTA  CGTCTCCGTC   360

TAGATTCCAG  TAGAATTATA  ATCATTGTTA  AAGTAGTATA  CAGTGTCATA  AATGGTTTTA   420

CATGCCATCC  ATGATTGGAT  GAGAGCCAAC  CAATGGGTCT  TACGTAATGG  ACAATGAAGC   480

ATTCGAGCCA  GGATGCATTT  AACGCAGCAA  GAGTCAGGCT  ACACAGGTGG  ATATCGATGT   540

TCACAACCGT  AAATCTAGAC  CCTTGAAGCT  CCACTGCCTA  TTCGAACAGG  CATTATGATT   600

TCAGGATGTC  TGCAGGACCC  TAGAAGGCGA  TTAGGCTGT   TTCGGAGATC  AATTCGGCTT   660

CCAAATCGCC  CACGGATGCT  CCACCGACTA  GGCTAAACCC  CATCACAGCG  GACGTTTCAG   720

GTACGGCAGG  GTCTCACATT  TAGGGCCTCG  GCAGGGTCTC  GGCAGGTACC  CTTCTTAATA   780

AAGGCTAAAT  AGCTTCTGCA  GAATCATGGG  TATATCAGGA  ACGTCTCCTC  CGTCGCTGCA   840

GACCTTCTCT  TCTTACTCCC  AGTCCCATTG  AATCAACTCC  TCAAGCCAAG  TCTCTTTCAA   900
```

```
C ATG CTT ACC AAG AAC CTT CTC CTC TGC TTC GCC GCA GCT AAG GCT           946
  Met Leu Thr Lys Asn Leu Leu Leu Cys Phe Ala Ala Ala Lys Ala
  1               5                   10                  15

GTT CTG GCC GTT CCC CAC GAC TCT GTC GTC GAG CGT TCC GAT GCC TTG         994
Val Leu Ala Val Pro His Asp Ser Val Val Glu Arg Ser Asp Ala Leu
                20                  25                  30

CAC AAG CTC TCT GAG CGT TCG ACC CCG AGC TCG ACC GGC GAG AAC AAC        1042
His Lys Leu Ser Glu Arg Ser Thr Pro Ser Ser Thr Gly Glu Asn Asn
            35                  40                  45

GGC TTC TAC TAC TCC TTC TGG ACC GAC GGC GGT GGT GAT GTG ACC TAC        1090
Gly Phe Tyr Tyr Ser Phe Trp Thr Asp Gly Gly Gly Asp Val Thr Tyr
        50                  55                  60

ACC AAC GGT GAC GCT GGC TCG TAC ACC GTC GAG TGG TCC AAC GTT GGC        1138
Thr Asn Gly Asp Ala Gly Ser Tyr Thr Val Glu Trp Ser Asn Val Gly
    65                  70                  75

AAC TTT GTT GGT GGA AAG GGC TGG AAC CCT GGA AGT GCG CAG                1180
Asn Phe Val Gly Gly Lys Gly Trp Asn Pro Gly Ser Ala Gln
80                  85                  90
```

```
TAAGTTAACC  TTTCCCAAGC  TGTCCCTCTA  GGGTATTCAG  TGAAACAAAT  GCTCACATAA  1240

CTTCAGG GAC ATC ACC TAC AGC GGC ACC TTC ACC CCT AGC GGC AAC GGC        1289
```

|     |     |     |     |     |     |     |     |     |     |     |     |     |     |     |     |
|---|---|---|---|---|---|---|---|---|---|---|---|---|---|---|---|
|     |     | Asp | Ile | Thr | Tyr | Ser | Gly | Thr | Phe | Thr | Pro | Ser | Gly | Asn | Gly |
|     |     |     | 95  |     |     |     | 100 |     |     |     |     | 105 |     |     |     |

| TAC | CTC | TCC | GTC | TAT | GGC | TGG | ACC | ACT | GAC | CCC | CTG | ATC | GAG | TAC | TAC | 1337 |
|---|---|---|---|---|---|---|---|---|---|---|---|---|---|---|---|---|
| Tyr | Leu | Ser | Val | Tyr | Gly | Trp | Thr | Thr | Asp | Pro | Leu | Ile | Glu | Tyr | Tyr |  |
|  |  | 110 |  |  |  | 115 |  |  |  |  | 120 |  |  |  |  |  |

| ATC | GTC | GAG | TCC | TAC | GGC | GAC | TAC | AAC | CCC | GGC | AGT | GGA | GGC | ACC | TAC | 1385 |
|---|---|---|---|---|---|---|---|---|---|---|---|---|---|---|---|---|
| Ile | Val | Glu | Ser | Tyr | Gly | Asp | Tyr | Asn | Pro | Gly | Ser | Gly | Gly | Thr | Tyr |  |
|  | 125 |  |  |  |  | 130 |  |  |  |  | 135 |  |  |  |  |  |

| AAG | GGC | ACC | GTC | ACC | TCC | GAT | GGA | TCC | GTC | TAC | GAT | ATC | TAC | ACG | GCT | 1433 |
|---|---|---|---|---|---|---|---|---|---|---|---|---|---|---|---|---|
| Lys | Gly | Thr | Val | Thr | Ser | Asp | Gly | Ser | Val | Tyr | Asp | Ile | Tyr | Thr | Ala |  |
| 140 |  |  |  |  | 145 |  |  |  |  | 150 |  |  |  |  | 155 |  |

| ACC | CGC | ACC | AAC | GCC | GCT | TCC | ATC | CAA | GGA | ACC | GCT | ACC | TTC | ACC | CAG | 1481 |
|---|---|---|---|---|---|---|---|---|---|---|---|---|---|---|---|---|
| Thr | Arg | Thr | Asn | Ala | Ala | Ser | Ile | Gln | Gly | Thr | Ala | Thr | Phe | Thr | Gln |  |
|  |  |  |  | 160 |  |  |  |  | 165 |  |  |  |  | 170 |  |  |

| TAC | TGG | TCC | GTT | CGC | CAG | AAC | AAG | AGA | GTC | GGA | GGA | ACT | GTT | ACC | ACT | 1529 |
|---|---|---|---|---|---|---|---|---|---|---|---|---|---|---|---|---|
| Tyr | Trp | Ser | Val | Arg | Gln | Asn | Lys | Arg | Val | Gly | Gly | Thr | Val | Thr | Thr |  |
|  |  |  | 175 |  |  |  |  | 180 |  |  |  |  | 185 |  |  |  |

| TCC | AAC | CAC | TTC | AAC | GCT | TGG | GCT | AAG | CTG | GGC | ATG | AAC | CTG | GGT | ACT | 1577 |
|---|---|---|---|---|---|---|---|---|---|---|---|---|---|---|---|---|
| Ser | Asn | His | Phe | Asn | Ala | Trp | Ala | Lys | Leu | Gly | Met | Asn | Leu | Gly | Thr |  |
|  |  | 190 |  |  |  |  | 195 |  |  |  |  | 200 |  |  |  |  |

| CAC | AAC | TAC | CAG | ATC | GTG | GCT | ACC | GAG | GGC | TAC | CAG | AGC | AGC | GGA | TCT | 1625 |
|---|---|---|---|---|---|---|---|---|---|---|---|---|---|---|---|---|
| His | Asn | Tyr | Gln | Ile | Val | Ala | Thr | Glu | Gly | Tyr | Gln | Ser | Ser | Gly | Ser |  |
| 205 |  |  |  |  | 210 |  |  |  |  |  | 215 |  |  |  |  |  |

| TCC | TCC | ATC | ACT | GTT | CAG | TGAGCTTGGA | TGTCCAACTG | TGCTTGCAGG | 1673 |
|---|---|---|---|---|---|---|---|---|---|
| Ser | Ser | Ile | Thr | Val | Gln |  |  |  |  |
| 220 |  |  |  |  | 225 |  |  |  |  |

| GATTGGGTGG | ATCTGGGAAA | TGAGTGCGAT | GGTCCTTGGA | AATATTGAGC | AATCATATGA | 1733 |
|---|---|---|---|---|---|---|
| TGTGTGAAAC | AATTAGTTGC | TCGCTATCAA | TGCACTTGTC | GTTGGAATCT | ATCAAGCCAT | 1793 |
| CTAGTGTAGT | ATCCTTCATA | CTCCGAGAAT | AGTACATTAC | AGACTATCTC | GGCAGATCGA | 1853 |
| GGCGCACCAC | TATCCGAGGG | ATACCTCTTT | TGGTCTAGTT | GTAGCAGTCT | GTGACATTAA | 1913 |
| CATCAAGTAT | TATGCGTGCT | AGCTCCCGTC | ATATTGTAGC | AGTCATTCCG | GAGTAGACGA | 1973 |
| CACCGGTTGG | TCGAGCCAAA | CTAAATGAGC | TATAATTTCA | ACAGCAGGAG | TCCGGACGGC | 2033 |
| GTCTGACCTC | AGTGATTCCA | GTAGGCATCT | TCTTTTACAC | GTTAGAGAAT | GTCTCAATTT | 2093 |
| CAGACAACCA | GCAATTATTC | ACATTCGGGA | TGTCCCACTT | ATCTCTTATG | ATCCTTCAAC | 2153 |
| ACGTCTACCA | ATGAAAGCCA | CTTTTTACTA | TGTAAGTAAA | AATCGACAAG | CCCGTCAGCG | 2213 |
| CCATGG |  |  |  |  |  | 2219 |

( 2 ) INFORMATION FOR SEQ ID NO:8:

( i ) SEQUENCE CHARACTERISTICS:
        ( A ) LENGTH: 225 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:8:

| Met | Leu | Thr | Lys | Asn | Leu | Leu | Leu | Cys | Phe | Ala | Ala | Ala | Lys | Ala | Val |
|---|---|---|---|---|---|---|---|---|---|---|---|---|---|---|---|
| 1 |  |  |  | 5 |  |  |  |  | 10 |  |  |  |  | 15 |  |

| Leu | Ala | Val | Pro | His | Asp | Ser | Val | Val | Glu | Arg | Ser | Asp | Ala | Leu | His |
|---|---|---|---|---|---|---|---|---|---|---|---|---|---|---|---|
|  |  |  | 20 |  |  |  |  | 25 |  |  |  |  | 30 |  |  |

| Lys | Leu | Ser | Glu | Arg | Ser | Thr | Pro | Ser | Ser | Thr | Gly | Glu | Asn | Asn | Gly |
|---|---|---|---|---|---|---|---|---|---|---|---|---|---|---|---|
|  |  | 35 |  |  |  |  | 40 |  |  |  |  | 45 |  |  |  |

| Phe | Tyr | Tyr | Ser | Phe | Trp | Thr | Asp | Gly | Gly | Gly | Asp | Val | Thr | Tyr | Thr |
|---|---|---|---|---|---|---|---|---|---|---|---|---|---|---|---|
|  | 50 |  |  |  |  | 55 |  |  |  |  | 60 |  |  |  |  |

| Asn | Gly | Asp | Ala | Gly | Ser | Tyr | Thr | Val | Glu | Trp | Ser | Asn | Val | Gly | Asn |

|     | 65 |     |     |     | 70  |     |     |     |     | 75  |     |     |     |     | 80  |
| --- | --- | --- | --- | --- | --- | --- | --- | --- | --- | --- | --- | --- | --- | --- | --- |
| Phe | Val | Gly | Gly | Lys 85 | Gly | Trp | Asn | Pro | Gly 90 | Ser | Ala | Gln | Asp | Ile 95 | Thr |
| Tyr | Ser | Gly | Thr 100 | Phe | Thr | Pro | Ser | Gly 105 | Asn | Gly | Tyr | Leu | Ser 110 | Val | Tyr |
| Gly | Trp | Thr 115 | Thr | Asp | Pro | Leu | Ile 120 | Glu | Tyr | Tyr | Ile | Val 125 | Glu | Ser | Tyr |
| Gly | Asp 130 | Tyr | Asn | Pro | Gly | Ser 135 | Gly | Gly | Thr | Tyr | Lys 140 | Gly | Thr | Val | Thr |
| Ser 145 | Asp | Gly | Ser | Val | Tyr 150 | Asp | Ile | Tyr | Thr | Ala 155 | Thr | Arg | Thr | Asn | Ala 160 |
| Ala | Ser | Ile | Gln | Gly 165 | Thr | Ala | Thr | Phe | Thr 170 | Gln | Tyr | Trp | Ser | Val 175 | Arg |
| Gln | Asn | Lys | Arg 180 | Val | Gly | Gly | Thr | Val 185 | Thr | Thr | Ser | Asn | His 190 | Phe | Asn |
| Ala | Trp | Ala 195 | Lys | Leu | Gly | Met | Asn 200 | Leu | Gly | Thr | His | Asn 205 | Tyr | Gln | Ile |
| Val | Ala 210 | Thr | Glu | Gly | Tyr | Gln 215 | Ser | Ser | Gly | Ser | Ser 220 | Ser | Ile | Thr | Val |
| Gln 225 |